United States Patent
Vandewall et al.

(10) Patent No.: US 10,647,433 B1
(45) Date of Patent: May 12, 2020

(54) PILLOW FOR PASSENGER SEAT OF A VEHICLE

(71) Applicant: THE BOEING COMPANY, Chicago, IL (US)

(72) Inventors: Cynthia A. Vandewall, Snohomish, WA (US); Swati Chopra, Dayton, OH (US); Brian Keller, Cincinnati, OH (US); Blake Lane, Cincinnati, OH (US); Shuai Mu, Shanxi (CN); Elizabeth O'Hearn, Cincinnati, OH (US); Chuyu Ruan, Guangdong (CN); Craig Vogel, Cincinnati, OH (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 16/188,340

(22) Filed: Nov. 13, 2018

(51) Int. Cl.
| | |
|---|---|
| *B64D 11/06* | (2006.01) |
| *B60N 2/885* | (2018.01) |
| *A47C 7/38* | (2006.01) |
| *A47G 9/10* | (2006.01) |
| *B60N 2/90* | (2018.01) |
| *A61B 5/0205* | (2006.01) |
| *A61B 5/00* | (2006.01) |

(52) U.S. Cl.
CPC ......... *B64D 11/0646* (2014.12); *A47C 7/383* (2013.01); *A47G 9/1027* (2013.01); *A47G 9/1081* (2013.01); *A61B 5/02055* (2013.01); *A61B 5/6802* (2013.01); *B60N 2/885* (2018.02); *B60N 2/914* (2018.02)

(58) Field of Classification Search
CPC ...... A47G 9/1027; A47G 9/1081; A47G 9/10; B64D 11/0646; B60N 2/885; A47C 7/383
See application file for complete search history.

(56) References Cited

U.S. PATENT DOCUMENTS

| | | | | |
|---|---|---|---|---|
| 7,013,512 B1 * | 3/2006 | Hsu | ...................... | A47G 9/1081 5/636 |
| 9,615,682 B1 * | 4/2017 | Maddocks | ............... | B60N 2/80 |
| 9,795,219 B1 * | 10/2017 | Gracie | ..................... | A47C 7/383 |
| 10,178,915 B1 * | 1/2019 | Sternlight | ............ | A47C 21/026 |
| 2001/0054837 A1 * | 12/2001 | O'Connor | .............. | A47C 7/383 297/397 |
| 2012/0313417 A1 * | 12/2012 | Hurwitz | ................. | B60N 2/882 297/391 |
| 2014/0020184 A1 * | 1/2014 | Loth | ..................... | A47G 9/1081 5/640 |
| 2014/0130261 A1 * | 5/2014 | Gumbrecht | ............ | A47C 7/383 5/644 |
| 2015/0197170 A1 * | 7/2015 | Obukhov | .............. | B60R 21/207 297/391 |
| 2016/0066716 A1 * | 3/2016 | Rao | ...................... | A47G 9/1036 5/644 |

(Continued)

FOREIGN PATENT DOCUMENTS

CA          3000331 A1 * 10/2018 ............. A47C 7/383

*Primary Examiner* — Timothy J Brindley
(74) *Attorney, Agent, or Firm* — The Small Patent Law Group LLC; Joseph M. Butscher

(57) ABSTRACT

A pillow includes a support body. A shape-adapting frame is within the support body. The shape-adapting frame is configured to be moved into and maintained in a desired position. At least one sensor is configured to detect at least one condition. The sensor(s) may be in communication with a monitoring control unit of a monitoring system.

20 Claims, 5 Drawing Sheets

(56) References Cited

U.S. PATENT DOCUMENTS

| | | | |
|---|---|---|---|
| 2016/0114708 A1* | 4/2016 | Spalter | B60N 2/882 |
| | | | 297/397 |
| 2017/0071349 A1* | 3/2017 | Wong | A47G 9/1081 |
| 2017/0143254 A1* | 5/2017 | Bell | A61B 5/11 |
| 2017/0173297 A1* | 6/2017 | Park | A47G 9/10 |
| 2018/0028001 A1* | 2/2018 | Wilmarth | A47G 9/1081 |
| 2018/0099754 A1* | 4/2018 | Erb | B64D 11/0647 |
| 2018/0137554 A1* | 5/2018 | Takahashi | A47G 9/0238 |
| 2018/0256387 A1* | 9/2018 | Anderson | A47G 9/1081 |
| 2018/0281638 A1* | 10/2018 | Chu | B60N 2/882 |
| 2018/0325292 A1* | 11/2018 | Kassab Arabo | A47G 9/066 |
| 2019/0061586 A1* | 2/2019 | Nakamura | B60N 2/885 |
| 2019/0069698 A1* | 3/2019 | Lin | A47G 9/1081 |
| 2019/0167020 A1* | 6/2019 | Bice | A47C 7/383 |

\* cited by examiner

PILLOW FOR PASSENGER SEAT OF A VEHICLE

FIELD OF THE DISCLOSURE

Embodiments of the present disclosure generally relate to pillows, and more particularly to pillows that are configured to be used with passenger seats of a vehicle, such as a commercial aircraft.

BACKGROUND OF THE DISCLOSURE

Commercial aircraft transport passengers between locations. During a flight, passengers within an aircraft are seated. A typical seat assembly within an internal cabin includes a headrest. A passenger may decide to rest and/or sleep during a flight. When passengers rest their heads on the headrest in an upright, seated position, the headrest may not be capable of maintaining the head in a stable position. For example, a passenger's head may slump to a side, which may awaken the passenger, who is trying to sleep.

Certain headrests on seats of a commercial aircraft include side flaps. However, the side flaps typically do not remain in position. As such, a head of a passenger in a seated position trying to rest may slide off or otherwise disengage from the headrest as the side flap moves to an undesirable position. For example, side flaps may be moved into a desired position by a passenger. However, as a head of a passenger leans on a side flap, the side flap typically flattens, which may cause a passenger's neck to kink and jar the passenger awake. In general, finding a comfortable resting position during a flight may prove a challenge to many individuals.

In general, certain passengers may not be able to attain sufficient rest during a flight. Indeed, certain passengers may become ill during a flight, such as due to motion sickness. However, flight attendants may only be aware of passenger discomfort when informed by the passenger. That is, a flight attendant may not know if a passenger is experiencing discomfort and/or sickness unless the passenger expressly tells the flight attendant.

SUMMARY OF THE DISCLOSURE

A need exists for a pillow that is configured to allow a passenger to be supported in a stable, comfortable position, such as during a flight of a commercial aircraft. Further, a need exists for a pillow that increases comfort and restfulness of an individual.

With those needs in mind, certain embodiments of the present disclosure provide a pillow including a support body. A shape-adapting frame is within the support body. The shape-adapting frame is configured to be moved into and maintained in a desired position. At least one sensor is configured to detect at least one condition.

The pillow may also include an inflatable membrane operatively coupled to a pump. The inflatable membrane is configured to be selectively inflated and deflated to adjust a desired amount of support for the pillow.

In at least one embodiment, the sensor(s) includes a biometric sensor that is configured to detect at least one biometric condition of an individual. In at least one embodiment, the sensor(s) includes an environmental sensor that is configured to detect at least one environmental condition surrounding an individual. The sensor(s) may be in communication with a monitoring control unit of a monitoring system.

The pillow may also include a stabilizer that is configured to stabilize the pillow with respect to a headrest. The stabilizer removably couples the pillow to the headrest to ensure that the pillow remains anchored thereto. The stabilizer may include one or more of a strap that is configured to removably loop onto a portion of the headrest, a clip that removably couples to a reciprocal portion of the headrest, one or more magnets within the support body that magnetically couple to reciprocal magnets of the portion of the headrest, one or more protuberances that removably couple to reciprocal members of the portion of the headrest, a hook and loop fastener that removably couples to a reciprocal hook and loop fastener of the headrest, and/or one or more buttons that are configured to removably couple to reciprocal members of the headrest. The pillow may integrally form a headrest of a seat assembly.

In at least one embodiment, the pillow includes a base and a neck cradle outwardly extending from the base. The base may include rounded lateral lobes connected together by a recessed intermediate joining section. A rear surface of the intermediate joining section inwardly recedes towards the neck cradle. The neck cradle may include lateral arms connected together by an inwardly curved cuff. The cuff inwardly curves towards the base. The lateral arms are configured to be selectively moved towards and away from a central lateral plane of the pillow. The neck cradle may include creases that are configured to provide adjustable movement of the lateral arms.

Certain embodiments of the present disclosure provide a passenger comfort system within a vehicle. The passenger comfort system includes a pillow including at least one sensor in communication with the monitoring control unit. The sensor(s) is configured to detect at least one condition. The passenger comfort system may also include a monitoring system having a monitoring control unit. The sensor(s) may be in communication with the monitoring control unit.

Certain embodiments of the present disclosure provide a pillow including a support body comprising a base having rounded lateral lobes connected together by a recessed intermediate joining section, and a neck cradle outwardly extending from the base. The neck cradle includes lateral arms connected together by an inwardly curved cuff. The cuff inwardly curves towards the base. The lateral arms are configured to be selectively moved towards and away from a central lateral plane of the pillow. A rear surface of the intermediate joining section inwardly recedes towards the neck cradle. A shape-adapting frame is within the support body. The shape-adapting frame is configured to be moved into and maintained in a desired position.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition may include additional elements not having that condition.

Certain embodiments of the present disclosure provide a pillow that is configured to support a passenger and promote resting and sleeping. In at least one embodiment, the pillow includes one or more sensors that are configured to detect conditions that may change as a passenger rests. At least one of the sensors may track the passenger vital signs and communicate with a monitoring system that informs a flight attendant regarding the passenger. In this manner, the pillow is able to automatically detect and communicate with the flight attendant that the passenger may be uncomfortable, sick, and/or the like, without the passenger expressly communicating with the flight attendant.

Embodiments of the present disclosure provide pillows that alleviate motion sickness, and may be customized to heads and necks of individuals. In at least one embodiment, the pillows have a wing-like shape, which allows for a more reliable resting spot that eliminates, minimizes, or otherwise reduces head slippage during a flight, for example. As such, the pillows increase passenger comfort, and consequently increase the cabin experience and customer satisfaction.

Figure 1:
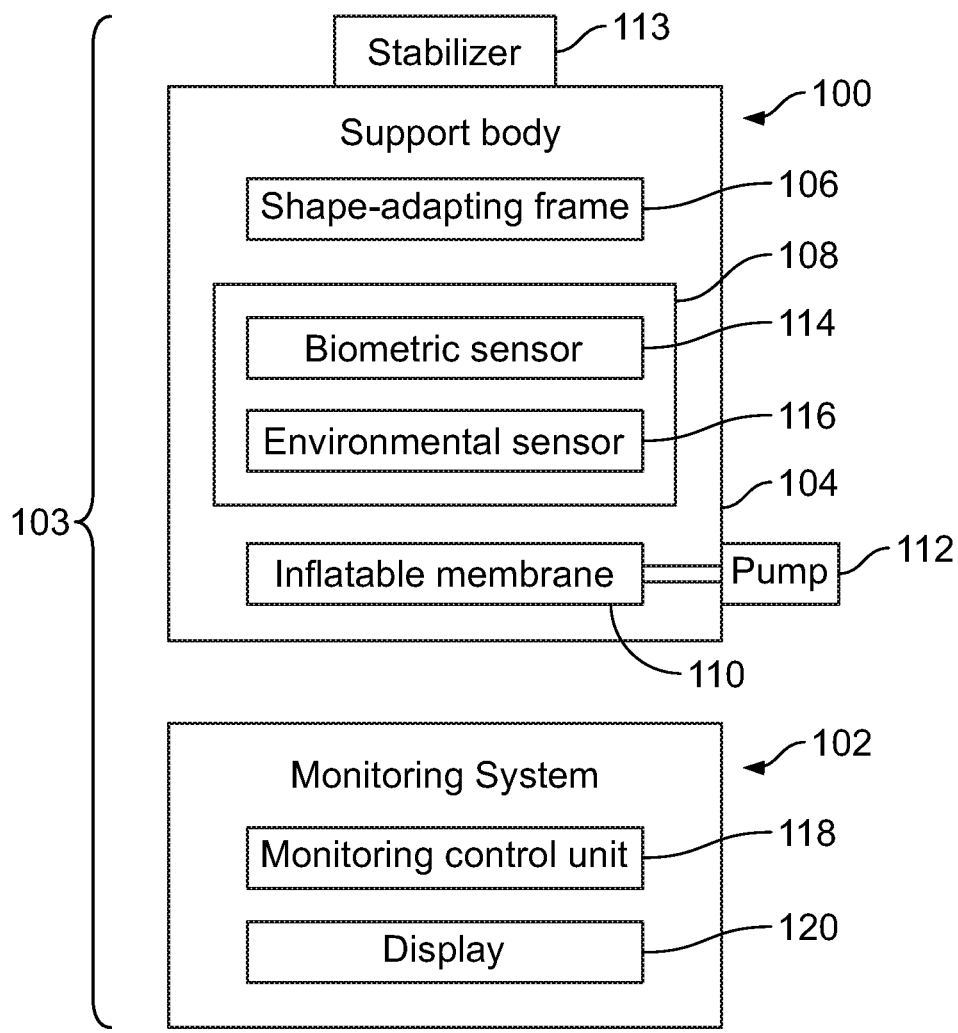
FIG. 1 illustrates a schematic block diagram of a pillow in communication with a monitoring system, according to an embodiment of the present disclosure.

FIG. 1 illustrates a schematic block diagram of a pillow 100 in communication with a monitoring system 102, according to an embodiment of the present disclosure. The pillow 100 and the monitoring system 102 provide a passenger comfort system 103 within a vehicle, which increases passenger comfort onboard a vehicle, such as a commercial aircraft. The pillow 100 includes a support body 104, such as a cushion, that retains a shape-adapting frame 106. One or more sensors 108 may be on and/or within the support body 104. The sensor(s) 108 is configured to detect one or more conditions, such as a biometric condition (for example, a vital sign) of an individual, or an environmental condition, such as a temperature surrounding the individual resting on the pillow 100. In at least one embodiment, an inflatable membrane 110 operatively coupled to a pump 112 may be within the support body 104. The pillow 100 may also include a stabilizer 113 that is configured to stabilize the pillow 100 with respect to another structure, such as a headrest of a seat assembly within a vehicle.

The support body 104 is an outer main structure. The support body 104 may include a soft material typically used for pillows, such as open cell foam, down, fill, and/or the like. The support body 104 may be covered with a fabric, such as linen, cloth, and/or the like.

The shape-adapting frame 106 provides an adaptable skeleton for the support body 104. The shape-adapting frame 106 is configured to be set and remain in a desired shape and/or position. For example, an individual may set the pillow 100 into a desired shape and/or position by manipulating the pillow 100, which causes the shape-adapting frame 106 to move in response thereto, and remain in the desired position until the individual decides to manipulate the pillow 100 into a different position. In at least one embodiment, the shape-adapting frame 106 is a thin metal wire frame that underlies the support body 104. Optionally, the shape-adapting frame 106 may include one or more thin metal panels that underlie the support body 104. As another example, the shape-adapting frame 106 may include a plurality of flexible and resilient beams, such as may be formed of metal, plastic or the like. The beams may be coupled together through flexible swivel joints. The shape-adapting frame 106 may be or include memory foam, gel, and/or the like.

The sensor(s) 108 may be or include one or more biometric sensors 114 and/or one or more environmental sensors 116. In at least one embodiment, the sensor(s) 108 may not include the environmental sensors 116. In at least one other embodiment, the sensor(s) 108 may not include the biometric sensors 114. In at least one embodiment, the pillow may alternatively not include any sensor(s) 108.

The sensors 108 may be in communication with a monitoring system 102, such as a computer within an internal cabin of an aircraft, a handheld device (such as a smart phone or tablet of an individual, such as a passenger onboard an aircraft and/or a flight attendant), and/or the like. The monitoring system 102 includes a monitoring control unit 118 that is in communication with the sensors 108 through wireless signals, such as Bluetooth, Wifi, or the like.

The biometric sensor(s) 114 is configured to detect at least one biometric condition of an individual resting on the pillow 100. For example, the biometric sensor(s) 114 may include a heart rate sensor, a body temperature sensor, and/or the like. In this manner, the biometric sensors 114 are configured to detect vital signs, such as heart rate, body temperature, or the like of an individual resting on the pillow 100 and communicate the vital sign information to the monitoring system 102. The monitoring control unit 118 may show such vital signs, such as on a display 120 (such as a monitor screen, touchscreen interface, and/or the like) in communication with the monitoring control unit 118. The monitoring control unit 118 may analyze the vital signs to determine if they are beyond normal thresholds and alert an individual at the monitoring system 102 that the passenger resting on the pillow 100 may be uncomfortable and/or sick.

The environmental sensor(s) 116 is configured to detect at least one environmental condition surrounding an individual resting on the pillow 100. For example, the environmental sensor(s) 116 may include a digital thermometer, humidistat, and/or the like that is configured to detect environmental conditions surround the passenger using the pillow 100. The environmental sensor 116 communicates the environmental information to the monitoring system 102. The monitoring control unit 118 analyzes the environmental information (such as environmental temperature, humidity, or the like). An individual (such as a flight attendant) may review the environmental information on the display 120. In this manner, the individual may assess the current environmental conditions surrounding the passenger independently of the passenger, and may adjust the environmental conditions if they are not conducive to resting. For example, a flight attendant may determine that the temperature surrounding the passenger is too high, and may adjust the temperature accordingly (such as through a thermostat, a fan, and/or the like on board an aircraft).

The inflatable membrane 110 may be formed of an elastomeric material, such as rubber, and configured to retain a fluid, such as air. The inflatable membrane 110 may be selectively inflated and deflated through operation of the pump 112. As such, the passenger may adjust a desired amount of support for the pillow via the pump 112 and the inflatable membrane. Optionally, the pillow 100 may not include the inflatable membrane 110 and the pump 112.

The stabilizer 113 is configured to securely anchor the pillow 100 with respect to another structure, such as a headrest of a seat assembly. In at least one embodiment, the stabilizer 113 includes a strap that is configured to removably loop onto a portion of the structure. As another example, the stabilizer 113 includes a clip that removably couples to a reciprocal portion of the structure. In at least one other embodiment, the stabilizer 113 may include one or more magnets within the support body that magnetically couple to reciprocal magnets within a portion of the structure. As another example, the stabilizer 113 may include one or more protuberances that removably couple to reciprocal members (such as slots, channels, tracks, and/or the like) within a portion of the structure. In at least one other embodiment, the stabilizer 113 is a hook and loop style fastener (such as Velcro) that removably couples to a reciprocal hook and loop style fastener on a portion of the structure. In at least one other embodiment, the stabilizer 113 includes snaps, buttons, or the like that are configured to removably couple to reciprocal members on a portion of the structure. The stabilizer 113 removably couples the pillow to the structure (such as the headrest of the seat assembly) to ensure that the pillow 100 remains anchored to the structure, and does not undesirably slide or otherwise move relative to the structure. Alternatively, the pillow 100 does not include the stabilizer 113.

In at least one other embodiment, the pillow 100 may be integrally formed with the other structure. For example, the pillow 100 may be or otherwise form a headrest of a seat assembly.

In operation, a passenger positions the pillow 100 on a structure, such as headrest, and adjusts the pillow to a desired position by manipulating the support body 104, which is moved in response thereto and maintained in the desired position via the shape-adapting frame 106. The pillow 100 may be anchored in position via the stabilizer 113. The passenger may adjust the support of the pillow via use of the pump 112 and the inflatable membrane 110.

As the passenger rests on the pillow, the sensors 108 detect biometric and/or environmental conditions. Sensor data is communicated to the monitoring control unit 118 of the monitoring system 102. A flight attendant may view the sensor data on the display 120 and determine if the passenger is experiencing discomfort (such as through biometric data), and/or if the environment is not conducive to resting (such as through environmental data). The flight attendant may then adjust conditions surrounding the passenger to alleviate any discomfort without the passenger expressly contacting the flight attendant.

As used herein, the term "control unit," "central processing unit," "unit," "CPU," "computer," or the like may include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms. For example, the monitoring control unit 118 may be or include one or more processors that are configured to control operation, as described herein.

The monitoring control unit 118 is configured to execute a set of instructions that are stored in one or more data storage units or elements (such as one or more memories), in order to process data. For example, the monitoring control unit 118 may include or be coupled to one or more memories. The data storage units may also store data or other information as desired or needed. The data storage units may be in the form of an information source or a physical memory element within a processing machine.

The set of instructions may include various commands that instruct the monitoring control unit 118 as a processing machine to perform specific operations such as the methods and processes of the various embodiments of the subject matter described herein. The set of instructions may be in the form of a software program. The software may be in various forms such as system software or application software. Further, the software may be in the form of a collection of separate programs, a program subset within a larger program or a portion of a program. The software may also include modular programming in the form of object-oriented programming. The processing of input data by the processing machine may be in response to user commands, or in response to results of previous processing, or in response to a request made by another processing machine.

The diagrams of embodiments herein may illustrate one or more control or processing units, such as the monitoring control unit 118. It is to be understood that the processing or control units may represent circuits, circuitry, or portions thereof that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the monitoring control unit 118 may represent processing circuitry such as one or more of a field programmable gate array (FPGA), application specific integrated circuit (ASIC), microprocessor(s), and/or the like. The circuits in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in a data storage unit (for example, one or more memories) for execution by a computer, including RAM memory, ROM memory, EPROM memory, EEPROM memory, and non-volatile RAM (NVRAM) memory. The above data storage unit types are exemplary only, and are thus not limiting as to the types of memory usable for storage of a computer program.

Figure 2:
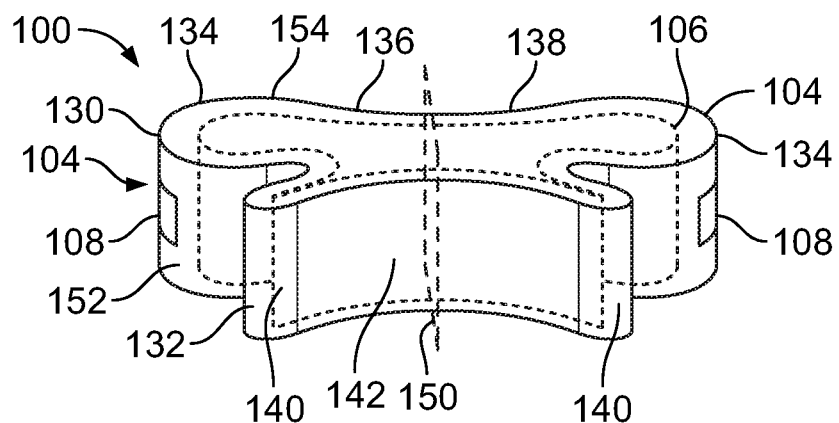
FIG. 2 illustrates a perspective front view of the pillow, according to an embodiment of the present disclosure.
Figure 3:
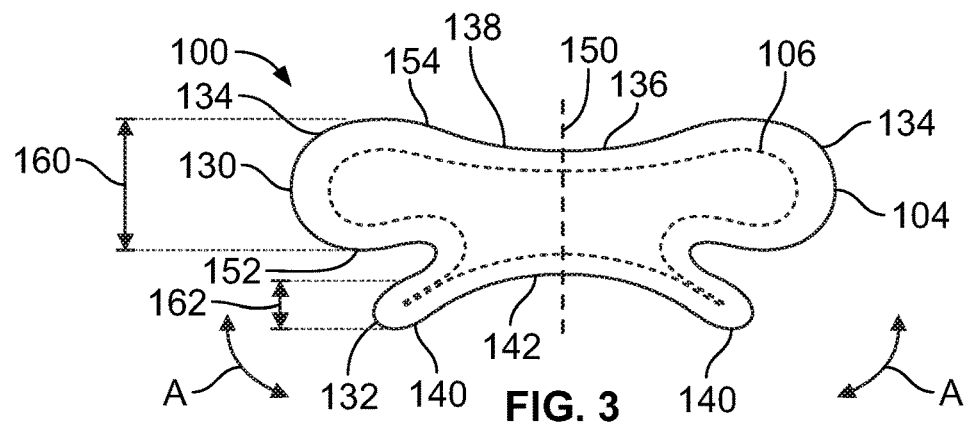
FIG. 3 illustrates a top view of the pillow of FIG. 2.

FIG. 2 illustrates a perspective front view of the pillow 100, according to an embodiment of the present disclosure. FIG. 3 illustrates a top view of the pillow 100 of FIG. 2.

Referring to FIG. 2, the shape-adapting frame 106 is contained within the support body 104 and allows an individual to manipulate and set a desired shape of the pillow 100.

The pillow 100 includes a base 130 and a neck cradle 132 outwardly extending from the base 130. The support body 104 includes the base 130 and the neck cradle 132. The shape-adapting frame 106 is within the support body 104. The shape-adapting frame 106 may extend through an entirety of the support body 104, including the base 130 and the neck cradle 132. The base 130 includes rounded lateral lobes 134 connected together by a recessed intermediate joining section 136. The lateral lobes 134 are expanded rounded members that are larger than the intermediate joining section 136. A rear surface 138 of the intermediate joining section 136 inwardly recedes towards the neck cradle 132. In this manner, the base 130 resembles a dumbbell-shape or dogbone-shape having outer lateral rounded sides (that is, the lobes 134) and a central section (that is, the recessed intermediate joining section 136) that smoothly connects to the rounded sides.

The neck cradle 132 includes lateral arms or wings 140 connected together by an inwardly curved cuff 142. The cuff 142 inwardly curves towards the base 130. The lateral arms 140 and the cuff 142 are configured to conform to a shape of a neck and/or portions of shoulders of an individual. The lateral arms 140 may be selectively pivoted towards and away from a central lateral plane 150 of the pillow in the directions of arc A. In this manner, an individual may selectively customize the neck cradle 132 to a desired supporting position. The shape-adapting frame 106 ensures that the neck cradle 132 remains in the desired position until the individual chooses to manipulate and change the desired position.

As shown, the lateral arms 140 outwardly extend from a front 152 of the base 130, while the cuff 142 inwardly recedes towards a rear 154 of the base 130. The lateral lobes 134 may extend further laterally than the lateral arms 140. The pillow 100 may be symmetrical in relation to the central lateral plane 150 before manipulation by a passenger. As the passenger manipulates the lateral arms 140 of the neck cradle 132, the pillow 100 may become asymmetrical in relation to the central lateral plane 150.

The base 130 includes a thickness 160 that exceeds a thickness 162 of the neck cradle 132. The lateral lobes 134 may be substantially thicker than the lateral arms 140. As such, the lateral arms 140 may be easier to manipulate into a desired position than the lateral lobes 134. The lateral arms 140 may be shorter or longer than shown.

The pillow 100 provides increased support to shoulders and a neck of an individual. For example, the neck cradle 132 may be customized and set to a desired neck support position of an individual. As such, the neck cradle 132 ensures that the head of an individual remains in an upright and stable position. The shoulders of the passenger may be supported by lower portions of the neck cradle and/or the lateral lobes 134 of the base 130, thereby ensuring comfort and support in a seated position.

As shown, the sensors 108 may be on or within the base 130. For example, the sensors 108 may be on the lateral lobes 134 or embedded therein. In at least one embodiment, one or more sensors 108 are embedded within the intermediate joining section 136.

Figure 4:
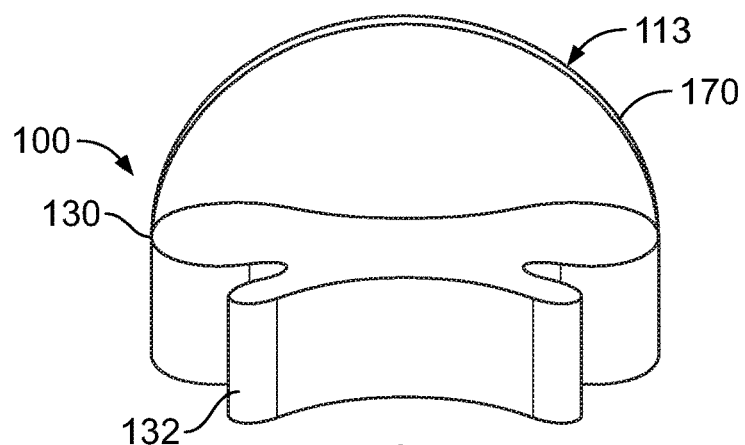
FIG. 4 illustrates a perspective front view of the pillow, according to an embodiment of the present disclosure.

FIG. 4 illustrates a perspective front view of the pillow, according to an embodiment of the present disclosure. In this embodiment, the stabilizer 113 is a strap 170 (such as string, rope, wire, or the like) extending from the base 130 of the pillow 100. The strap 170 is configured to securely anchor the pillow 100 with respect to a headrest of a seat assembly. For example, the strap 170 may loop around an upper portion of the headrest. The strap 170 is configured to removably loop onto a portion of the headrest.

Figure 5:
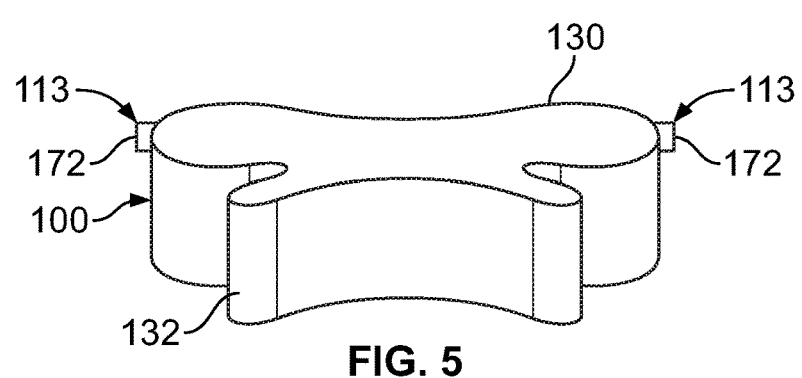
FIG. 5 illustrates a perspective front view of the pillow, according to an embodiment of the present disclosure.

FIG. 5 illustrates a perspective front view of the pillow 100, according to an embodiment of the present disclosure. In this embodiment, the stabilizer 113 includes one or more clips 172 extending from the base 130. The clips 172 are configured to removably couple to reciprocal clips, recesses, clasps, or the like of a headrest.

Figure 6:
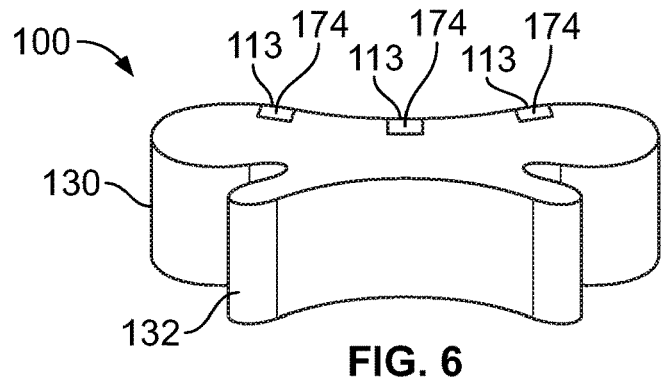
FIG. 6 illustrates a perspective front view of the pillow, according to an embodiment of the present disclosure.

FIG. 6 illustrates a perspective front view of the pillow 100, according to an embodiment of the present disclosure. In this embodiment, the stabilizer 113 includes one or more magnets 174, such as embedded within the base 130. The magnets 174 are configured to magnetically couple to reciprocal magnets within a headrest.

Figure 7:
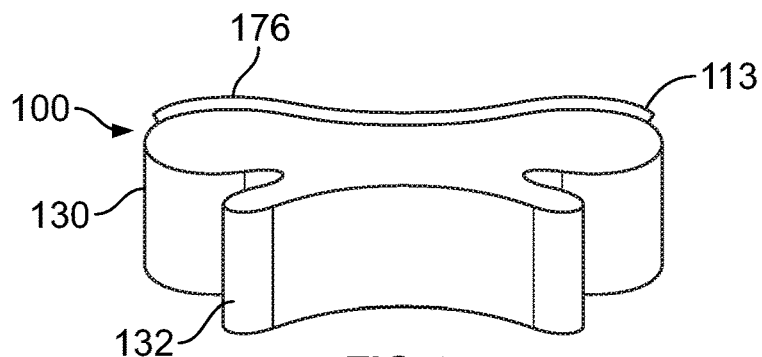
FIG. 7 illustrates a perspective front view of the pillow, according to an embodiment of the present disclosure.

FIG. 7 illustrates a perspective front view of the pillow 100, according to an embodiment of the present disclosure. The stabilizer 113 may be or include one or more protuberances, such as a rail 176, which removably couples to a reciprocal slot, channel, or track of a headrest.

Figure 8:
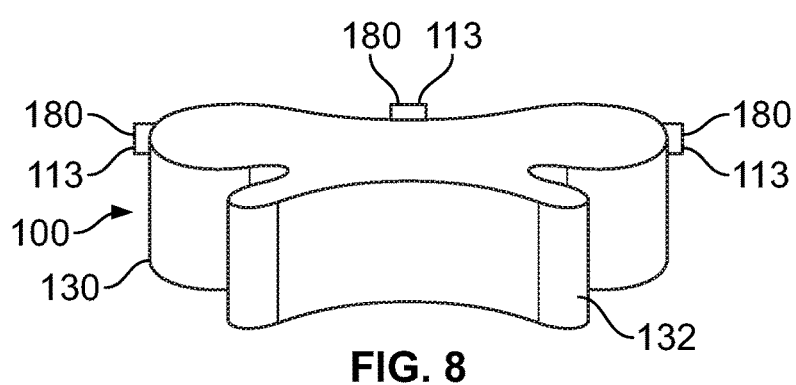
FIG. 8 illustrates a perspective front view of the pillow, according to an embodiment of the present disclosure.

FIG. 8 illustrates a perspective front view of the pillow 100, according to an embodiment of the present disclosure. The stabilizer 113 may be or include one or more hook and loop fasteners 180 that removably couple to reciprocal hook and loop fasteners of a headrest.

Figure 9:
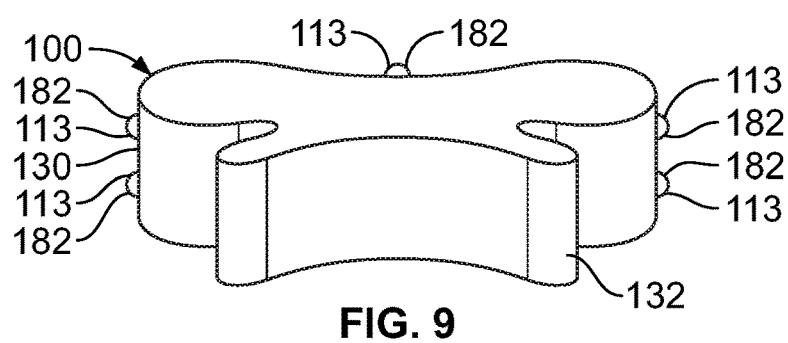
FIG. 9 illustrates a perspective front view of the pillow, according to an embodiment of the present disclosure.

FIG. 9 illustrates a perspective front view of the pillow 100, according to an embodiment of the present disclosure. In this embodiment, the stabilizer 113 includes buttons 182 that are configured to removably couple to reciprocal button members on headrest.

Figure 10:
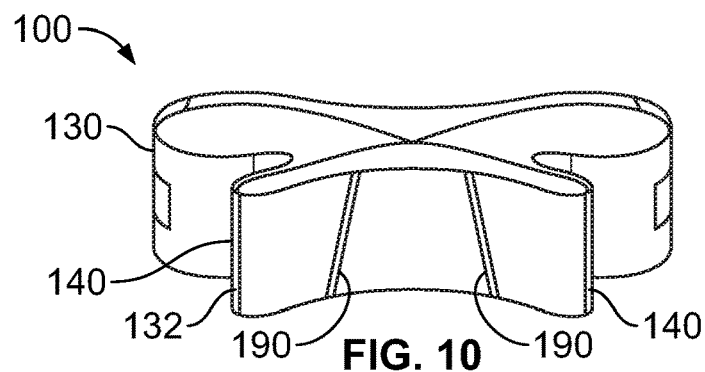
FIG. 10 illustrates a perspective front view of the pillow, according to an embodiment of the present disclosure.

FIG. 10 illustrates a perspective front view of the pillow 100, according to an embodiment of the present disclosure. The neck cradle 132 may include linear creases 190 that are configured to allow the lateral arms 140 to pivot thereabout. As such, the lateral rams 140 may be moved about the creases in a flap-like manner. Any of the embodiments of the present disclosure may include the creases 190.

Figure 11:
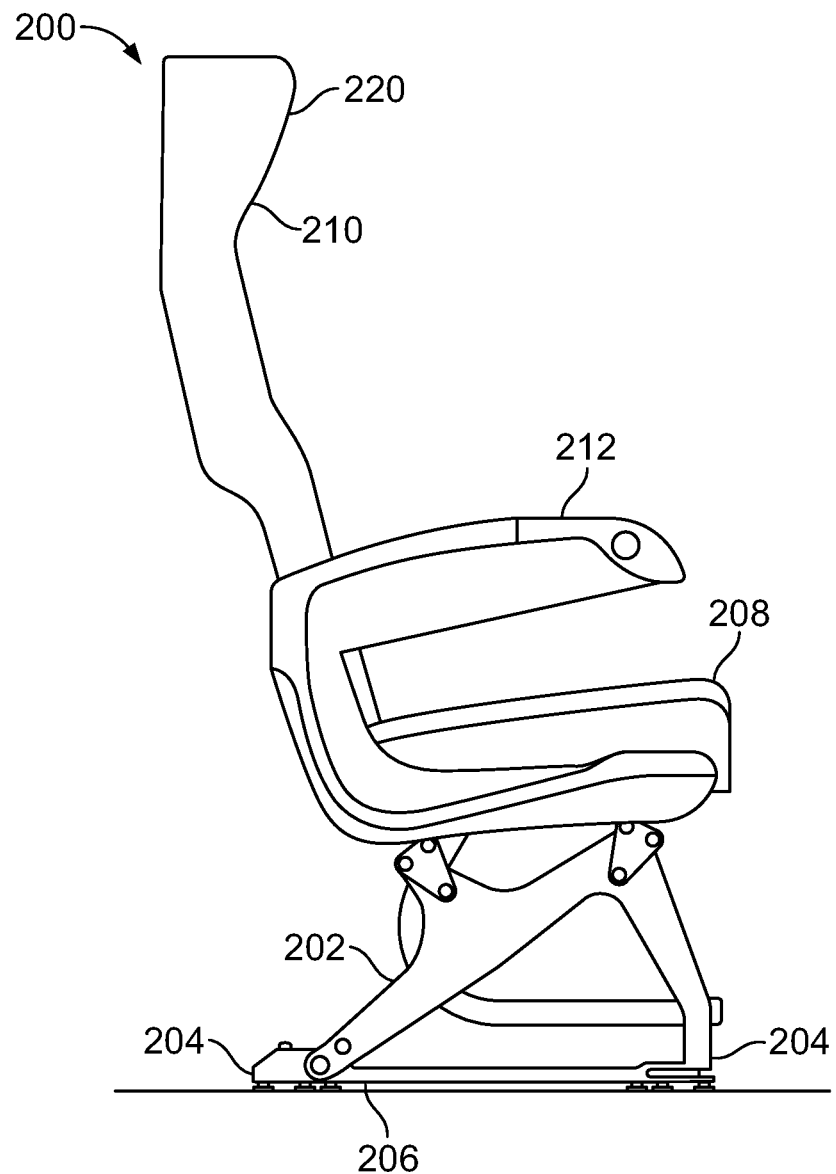
FIG. 11 illustrates a side view of a seat assembly.

FIG. 11 illustrates a side view of a seat assembly 200. In at least one embodiment, the seat assembly 200 may be configured to be secured within an interior cabin of a vehicle, such as a commercial aircraft.

The seat assembly 200 includes a base 202, which may include legs 204 that may be secured to tracks 206 within an interior cabin of a vehicle. The legs 204 may include fittings, fasteners, or the like that are configured to securely connect the legs 204 to the tracks 206. The base 202 supports a seat cushion 208 and a backrest 210, which includes a headrest 220. Armrests 212 may be pivotally secured to the backrest 210 and/or the base 202.

Referring to FIGS. 1-11, the pillow 100 is positioned on the headrest 220 to provide an individual with increased comfort and support, as described herein. The pillow 100 may be securely anchored to the headrest via the stabilizer 113. In at least one embodiment, the pillow 100 may integrally form the headrest 220. That is, the headrest 220 may be or otherwise include the pillow 100.

Figure 12:
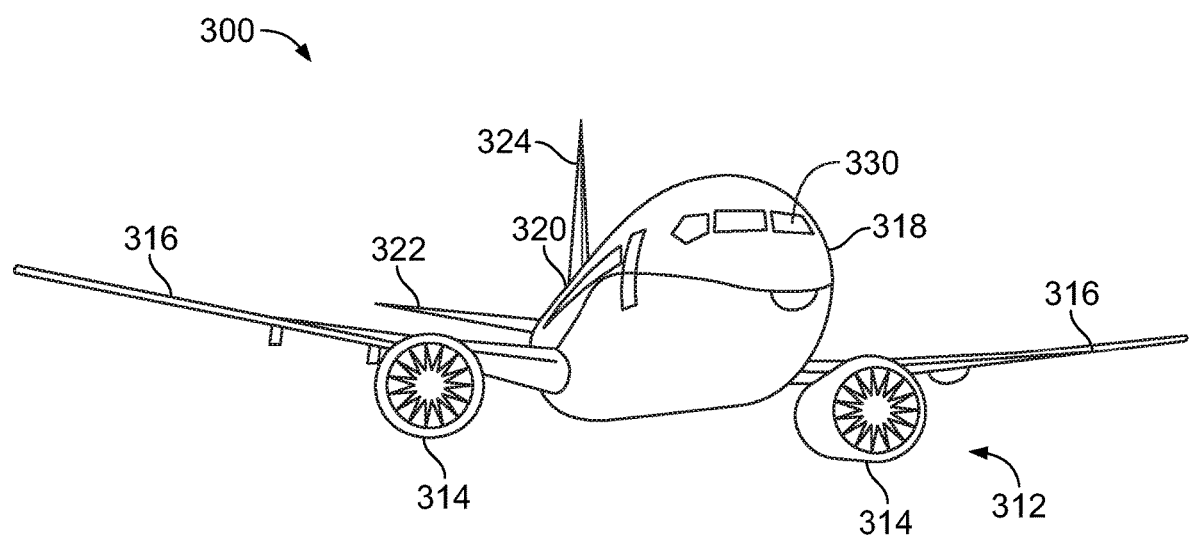
FIG. 12 illustrates a front perspective view of an aircraft.

FIG. 12 illustrates a front perspective view of an aircraft 300. The aircraft 300 includes a propulsion system 312 that may include two turbofan engines 314, for example. Optionally, the propulsion system 312 may include more engines 314 than shown. The engines 314 are carried by wings 316 of the aircraft 300. In other embodiments, the engines 314 may be carried by a fuselage 318 and/or an empennage 320. The empennage 320 may also support horizontal stabilizers 322 and a vertical stabilizer 324. The fuselage 318 of the aircraft 300 defines an internal cabin, which may include a cockpit 330.

The passenger comfort system 103 shown in FIG. 1 may be used within the aircraft 300, or various other vehicles. Passengers are seated on seat assemblies, such as the seat assembly 200 shown in FIG. 11, within the internal cabin. The passengers may be supported by the pillows 100 on the seat assemblies 200, as shown and described with respect to FIGS. 1-11. The aircraft 300 may be sized, shaped, and configured other than shown in FIG. 12.

Embodiments of the present disclosure may be used with various other vehicles other than aircraft. For example, the pillows 100 may be used with seat assemblies of land-based vehicles, water-based vehicles, or space-based vehicles. Further, embodiments of the present disclosure may be used in settings other than with vehicles. For example, individuals may use the pillows 100 with respect to seats, couches, beds, or the like in fixed structures (such as residences, office buildings, and/or the like).

As described herein, embodiments of the present disclosure provide pillows that are configured to allow an individual to be supported in a stable, comfortable position, such as during a flight of a commercial aircraft. Further, embodiments of the present disclosure provide pillows that increase comfort and restfulness of an individual.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

The invention claimed is:

1. A pillow comprising:
a support body including a base including rounded lateral lobes connected together by a recessed intermediate joining section, and a neck cradle in front of and outwardly extending from the base wherein the neck cradle comprises lateral arms connected together by an inwardly curved cuff, wherein the cuff inwardly curves towards the base, wherein the lateral lobes of the base extend further laterally than the lateral arms of the neck cradle, wherein the lateral arms are configured to be selectively moved towards and away from a central lateral plane of the pillow, and wherein a rear surface of the intermediate joining section inwardly recedes towards the neck cradle;
a shape-adapting frame within the support body, wherein the shape-adapting frame is configured to be moved into and maintained in a desired position; and
a biometric sensor that is configured to detect at least one biometric condition of an individual.

2. The pillow of claim 1, further comprising an inflatable membrane operatively coupled to a pump, wherein the inflatable membrane is configured to be selectively inflated and deflated to adjust a desired amount of support for the pillow.

3. The pillow or claim 1, further comprising an environmental sensor that is configured to detect at least one environmental condition surrounding an individual.

4. The pillow of claim 1, wherein the biometric sensor is in communication with a monitoring control unit of a monitoring system.

5. The pillow of claim 1, further comprising a stabilizer that is configured to stabilize the pillow with respect to a headrest, wherein the stabilizer removably couples the pillow to the headrest to ensure that the pillow remains anchored thereto.

6. The pillow of claim 5, wherein the stabilizer comprises one or more of a strap that is configured to removably loop onto a portion of the headrest, a clip that removably couples to a reciprocal portion of the headrest, one or more magnets within the support body that magnetically couple to reciprocal magnets of the portion of the headrest, one or more protuberances that removably couple to reciprocal members of the portion of the headrest, a hook and loop fastener that removably couples to a reciprocal hook and loop fastener of the headrest, or one or more buttons that are configured to removably couple to reciprocal members of the headrest.

7. The pillow of claim 1, wherein the pillow integrally forms a headrest of a seat assembly.

8. The pillow of claim 1, wherein the neck cradle further includes creases that are configured to provide adjustable movement of the lateral arms.

9. The pillow of claim 1, wherein the biometric sensor is within the support body.

10. A passenger comfort system within a vehicle, the passenger comfort system comprising:
a pillow including:
 a base including rounded lateral lobes connected together by a recessed intermediate joining section; and
 a neck cradle in front of and outwardly extending from the base, wherein the neck cradle comprises lateral arms connected together by an inwardly curved cuff, wherein the cuff inwardly curves towards the base, wherein the lateral lobes of the base extend further laterally than the lateral arms of the neck cradle, wherein the lateral arms are configured to be selectively moved towards and away from a central lateral plane of the pillow, and wherein a rear surface of the intermediate joining section inwardly recedes towards the neck cradle; and
a biometric sensor, wherein the biometric sensor is configured to detect at least one biometric condition of an individual.

11. The passenger comfort system of claim 10, further comprising a monitoring system including a monitoring control unit, wherein the biometric sensor is in communication with the monitoring control unit.

12. The passenger comfort system of claim 10, wherein the pillow further comprises a shape-adapting frame configured to be moved into and maintained in a desired position.

13. The passenger comfort system of claim 10, wherein the pillow further comprises an environmental sensor that is configured to detect at least one environmental condition surrounding an individual.

14. The passenger comfort system of claim 10, wherein the pillow further comprises a stabilizer that is configured to stabilize the pillow with respect to a headrest, wherein the stabilizer removably couples the pillow to the headrest to ensure that the pillow remains anchored thereto.

15. The passenger comfort system of claim 10, wherein the biometric sensor is within a support body of the pillow.

16. The passenger comfort system of claim 10, wherein the pillow integrally forms a headrest of a seat assembly.

17. The passenger comfort system of claim 14, wherein the stabilizer comprises one or more of a strap that is configured to removably loop onto a portion of the headrest, a clip that removably couples to a reciprocal portion of the headrest, one or more magnets within the support body that magnetically couple to reciprocal magnets of the portion of the headrest, one or more protuberances that removably couple to reciprocal members of the portion of the headrest, a hook and loop fastener that removably couples to a reciprocal hook and loop fastener of the headrest, or one or more buttons that are configured to removably couple to reciprocal members of the headrest.

18. A pillow comprising:
a support body including:
 a base including rounded lateral lobes connected together by a recessed intermediate joining section; and
 a neck cradle in front of and outwardly extending from the base, wherein the neck cradle includes lateral arms connected together by an inwardly curved cuff, wherein the cuff inwardly curves towards the base, wherein the lateral lobes of the base extend further laterally than the lateral arms of the neck cradle, wherein the lateral arms are configured to be selectively moved towards and away from a central lateral plane of the pillow, and wherein a rear surface of the intermediate joining section inwardly recedes towards the neck cradle; and
a shape-adapting frame within the support body, wherein the shape-adapting frame is configured to be moved into and maintained in a desired position.

19. The pillow of claim 18, further comprising an inflatable membrane operatively coupled to a pump, wherein the inflatable membrane is configured to be selectively inflated and deflated to adjust a desired amount of support for the pillow.

20. The pillow of claim 18, wherein the neck cradle further includes creases that are configured to provide adjustable movement of the lateral arms.

* * * * *